(12) United States Patent
Tomoeda

(10) Patent No.: US 10,719,796 B2
(45) Date of Patent: Jul. 21, 2020

(54) METHODS AND SYSTEMS FOR DETECTING AN ABNORMAL STRESS CONDITION IN A SUBJECT OR GROUP OF SUBJECTS

(71) Applicant: IMATEC INC., Chiba-ken (JP)

(72) Inventor: Atsushi Tomoeda, Tokyo (JP)

(73) Assignee: IMATEC INC., Matsudo-Shi, Chiba-Ken (JP)

( * ) Notice: Subject to any disclaimer, the term of this patent is extended or adjusted under 35 U.S.C. 154(b) by 513 days.

(21) Appl. No.: 15/214,397

(22) Filed: Jul. 19, 2016

(65) Prior Publication Data

US 2017/0004425 A1 Jan. 5, 2017

Related U.S. Application Data

(62) Division of application No. 13/643,953, filed as application No. PCT/JP2011/060225 on Apr. 27, 2011, now abandoned.

(30) Foreign Application Priority Data

Apr. 30, 2010 (JP) ................................. 2010-105882

(51) Int. Cl.
*G06Q 10/06* (2012.01)
*A61B 5/16* (2006.01)
*G06F 19/00* (2018.01)

(52) U.S. Cl.
CPC ......... *G06Q 10/0635* (2013.01); *A61B 5/165* (2013.01); *G06F 19/3418* (2013.01); *G06Q 10/06* (2013.01); *G06Q 10/063* (2013.01)

(58) Field of Classification Search
CPC .. G06Q 10/0635; G06Q 10/06; G06Q 10/063; G06F 19/3418; A61B 5/165
See application file for complete search history.

(56) References Cited

U.S. PATENT DOCUMENTS 5,615,138 A * 3/1997 Tanaka .................. G06Q 10/06
702/81
2001/0049471 A1 12/2001 Suzuki
(Continued)

FOREIGN PATENT DOCUMENTS

CN 1745698 3/2006
CN 101264012 9/2008
(Continued)

OTHER PUBLICATIONS

From U.S. Appl. No. 13/643,953 (published as US 2013-0041715 A1), Office Action dated Feb. 19, 2016.
(Continued)

*Primary Examiner* — Sujay Koneru
(74) *Attorney, Agent, or Firm* — Ladas & Parry, LLP

(57) ABSTRACT

Disclosed are methods and systems for detecting an abnormal stress condition in a subject or group of subjects. Included is a risk evaluation system monitoring people, wherein a control unit in a stress management system obtains mental health information and records same in a measurement information database. The control unit then specifies a pattern in a reference pattern database and obtains the measurement information relating to this pattern from the measurement information database. The control unit in the stress management system (20) then revises a standard pattern based on individual attributes or work attributes. Next, the control unit performs pattern matching and determines whether or not attention is required. If the determination is that attention is required, the control unit presents an alert and an advice. This enables work, organization, and member risks to be appropriately evaluated based on changes in mental health information.

6 Claims, 7 Drawing Sheets

(56) References Cited

U.S. PATENT DOCUMENTS

| | | | |
|---|---|---|---|
| 2006/0015377 A1 | 1/2006 | Hoogs | |
| 2007/0276714 A1 | 11/2007 | Beringer | |
| 2008/0091515 A1 | 4/2008 | Thieberger | |
| 2008/0109271 A1* | 5/2008 | Smith | G06Q 10/06 700/97 |
| 2008/0146895 A1 | 6/2008 | Olson | |
| 2009/0192843 A1* | 7/2009 | Ayala | G06Q 10/06 705/7.42 |
| 2010/0021873 A1* | 1/2010 | Stut | G06F 19/00 434/236 |
| 2010/0131607 A1 | 5/2010 | Firminger | |
| 2010/0228584 A1* | 9/2010 | Nash | G06Q 10/00 705/7.42 |
| 2011/0125547 A1* | 5/2011 | Brdiczka | G06Q 10/06 705/7.26 |
| 2013/0041715 A1 | 2/2013 | Tomoeda | |

FOREIGN PATENT DOCUMENTS

| | | |
|---|---|---|
| CN | 101520815 | 9/2009 |
| JP | 08-275934 | 10/1996 |
| JP | 10-071137 | 3/1998 |
| JP | 2001-344352 | 12/2001 |
| JP | 2002-228657 | 8/2002 |
| JP | 2004-008573 | 1/2004 |
| JP | 2005-122339 | 5/2005 |
| JP | 2005-188969 | 7/2005 |
| JP | 2005-334205 | 8/2005 |
| JP | 2009-110490 | 5/2009 |
| JP | 2010-003070 | 1/2010 |

OTHER PUBLICATIONS

From U.S. Appl. No. 13/643,953 (published as US 2013-0041715 A1), Office Action dated Oct. 22, 2015.
From U.S. Appl. No. 13/643,953 (published as US 2013-0041715 A1), Office Action dated Feb. 25, 2015.
From U.S. Appl. No. 13/643,953 (published as US 2013-0041715 A1), Office Action dated Oct. 19, 2014.
PCT International Preliminary Report on Patentability Chapter I from PCT/JP2011/060225 dated Dec. 10, 2012, and its English translation.
PCT Written Opinion of the International Search Authority from PCT/JP2011/060225 dated Jul. 12, 2011, and its English translation.
PCT International Search Report from PCT/JP2011/060225 dated Jul. 12, 2011, and its English translation.
Extended European Search Report dated Dec. 22, 2014 from corresponding European Patent Application No. 11775034.9.
Office action from Chinese Patent Application No. 201180022667.6 dated Mar. 19, 2015, and its English translation (Global Dossier, ESPACENET).
Research Institute of Human Engineering for Quality Life, "Research report regarding applicability of stress measurement technique to safety measures", [online], Mar. 2004, The Mechanical Social Systems Foundation, [Search on Apr. 12, 2010. Internet <URL: http://www.hql.jp /research/before/pdf/stress2003.pdf> English translation from Google Translate Toolkit is provided for this document.

* cited by examiner

METHODS AND SYSTEMS FOR DETECTING AN ABNORMAL STRESS CONDITION IN A SUBJECT OR GROUP OF SUBJECTS

CROSS-REFERENCE TO RELATED APPLICATIONS

This application is a Divisional Application of U.S. patent application Ser. No. 13/643,953 entitled "Risk Evaluation System Using People as Sensors" and filed on Oct. 26, 2012, which is a US National Stage of International Patent Application No. PCT/JP2011/060225 filed on Apr. 27, 2011, which claims priority to Japanese Patent Application No. 2010-105882 filed on Apr. 30, 2010, the disclosures of which are incorporated by reference in their entireties.

TECHNICAL FIELD

The present invention relates to methods and systems for detecting an abnormal stress condition in a subject or group of subjects as well as a risk evaluation system for perceiving the risk status of business operations, organizations and members by using each person as a sensor through observation of transition made in mental metrics such as the stress level of members involved in an organization and/or a business operation.

BACKGROUND ART

The measurement of stress has been carried out in order to understand health and mental conditions as well as for other medical purposes. There has been a technique studied to realize reduction of mental stress by collecting data such as physiological quantity, subject quantity, behavior quantity and environmental parameters and analyzing a correlation among the collected data (e.g. see Patent Document 1). According to the technique described in this document, physiological reaction of a subject is measured in a physiological reaction measurement processor and the physiological reaction is used to obtain a physical index in a physiological indicator extractor. Next, the physiological index is converted into a living body parameter in a physiological quantity evaluation determination unit using a physiological model so that the living body parameter obtained through the conversion is compared to a preset pattern. Then, if these patterns match each other, a subject quantity data collector is made to collect a subject quantity of the subject.

There has also been a technique studied for providing a psychological test adapted to each social role (in the office, school or family) through the Internet for determination of the latent mental health of users (e.g. see Patent Document 2). According to the technique described in this document, a stress state in each social role is analyzed and grounds for the cause/process of unsoundness are presented to implement psychological support contents such as counseling for solving the issue.

A research has also been carried out for the actual state of the stress of general public and the relationship between work accidents and the stress (e.g. see Non-Patent Document 1). In the study of this research, measurement techniques to allow easy stress measurement in daily life are enumerated such as measurement of physiological index (i.e. biological information), subjective/cognitive reaction and behavior reaction.

PRIOR ART DOCUMENTS

Patent Documents

Patent Document 1: Japanese Laid-Open Patent Publication No. 8-275934 (page 1, FIG. 1)
Patent Document 2: Japanese Laid-Open Patent Publication No. 2009-110490 (page 1, FIG. 1)

Non-Patent Document

Non-patent document 1: Research Institute of Human Engineering for Quality Life "Research report regarding applicability of stress measurement technique to safety measures", [online], March 2004, The Mechanical Social Systems Foundation, [Searched on Apr. 12, 2010] Internet <URL: http://www.hql.jp/research/before/pdf/stress2003.pdf>

SUMMARY OF THE INVENTION

Problems that the Invention is to Solve

If a member engaged in a business operation suffers from mental damage such as stress, a leave of absence and troubles may result in seriously affecting productivity and/or continuity of the business operation. Depending on a circumstance of the business operation, it may cause serious mental damage to members who are engaged in the business operation.

Although measures have been taken to mitigate the above risk by measurement of mental information such as stress of employees and/or members who are engaged in a business operation, absolute evaluation is difficult to obtain because mental information depends on the personality and temperament of subjects and is susceptible to a situation at the time of measurement. Accordingly, it is difficult to predict a risk based on the mental stress of each subject, which is based on mental information at one point.

In addition, in risk evaluation of contents of a business operation, management and inspection are often carried out based on reports and material concerning the business operation. However, this method may not determine whether a current business operation is good or poor. For example, even with excellent report contents, a business operation may be in a critical condition. Also, business inspection is often carried out subsequently, which does not necessarily enable risk evaluation in real time.

Accordingly, it is an objective of the present invention is to provide a risk evaluation system for evaluating the risk of business operations, organizations and members in real time based on transition of mental information of users.

Means for Solving the Problems

To solve the above problems, the present invention provides a risk evaluation system comprising: measurement information storage means for storing mental information of each user time-sequentially; pattern information storage means for storing a reference pattern serving as information of transition of the mental information; and control means connected to measurement means for the mental information and output means. The control means includes: means for obtaining mental information of each user from the measurement means to register the obtained mental information in the measurement information storage means; means for obtaining, from the pattern information storage means, a reference pattern relating to transition of the mental information; means for comparing, to the reference pattern, transition of the mental information recorded in the measurement information storage means; and means for outputting an alarm to the output means based on the comparison result.

According to the present invention, a reference pattern regarding transition of mental information is obtained and the reference pattern is compared to transition of mental information recorded in measurement information storage means. Therefore, an abnormal condition of mental stress is detected based on a change and the risk state of business operations, organizations and members can be detected by using each person as a sensor.

The risk evaluation system according to the present invention may further comprise user attribute information storage means for storing attribute information of each user. The control means further comprises means for obtaining the attribute information of each user and correcting a comparison method based on the attribute information.

According to the above configuration, stress tolerance or other factors of users can be taken into consideration for risk evaluation corresponding to the above attributes.

The risk evaluation system according to the present invention may further comprise business management information storage means for storing constituent information of a business operation and each user engaged in the business operation. The control means includes: means for calculating a statistic of mental information of each user based on the constituent information; means for obtaining reference patterns relating to each user and transition of the statistic based on the constituent information; means for comparing transition of the statistic of the mental information and the reference pattern; and means for outputting an alarm for the business operation based on the comparison result.

According to the above configuration, mental information of a plurality of users can be used as a basis for risk evaluation of a business operation that is an aggregate of the users.

The risk evaluation system according to the present invention may further comprise business attribute information storage means for storing attribute information of each business operation. The control means further includes means for obtaining the attribute information of each business operation and correcting a comparison method based on the attribute information.

According to the above configuration, the nature of business operations can be taken into consideration for risk evaluation.

The risk evaluation system according to the present invention may further comprise means for comparing transition of the statistic and transition of each user engaged in the business operation; and means for outputting an alarm for each user based on the comparison result.

According to the above configuration, a user to whom attention should be paid can be identified in a business operation carried out by a group.

As stated above, the present invention makes it possible to realize risk evaluation based on transition of mental information of users.

MODES FOR CARRYING OUT THE INVENTION

Figure 1:
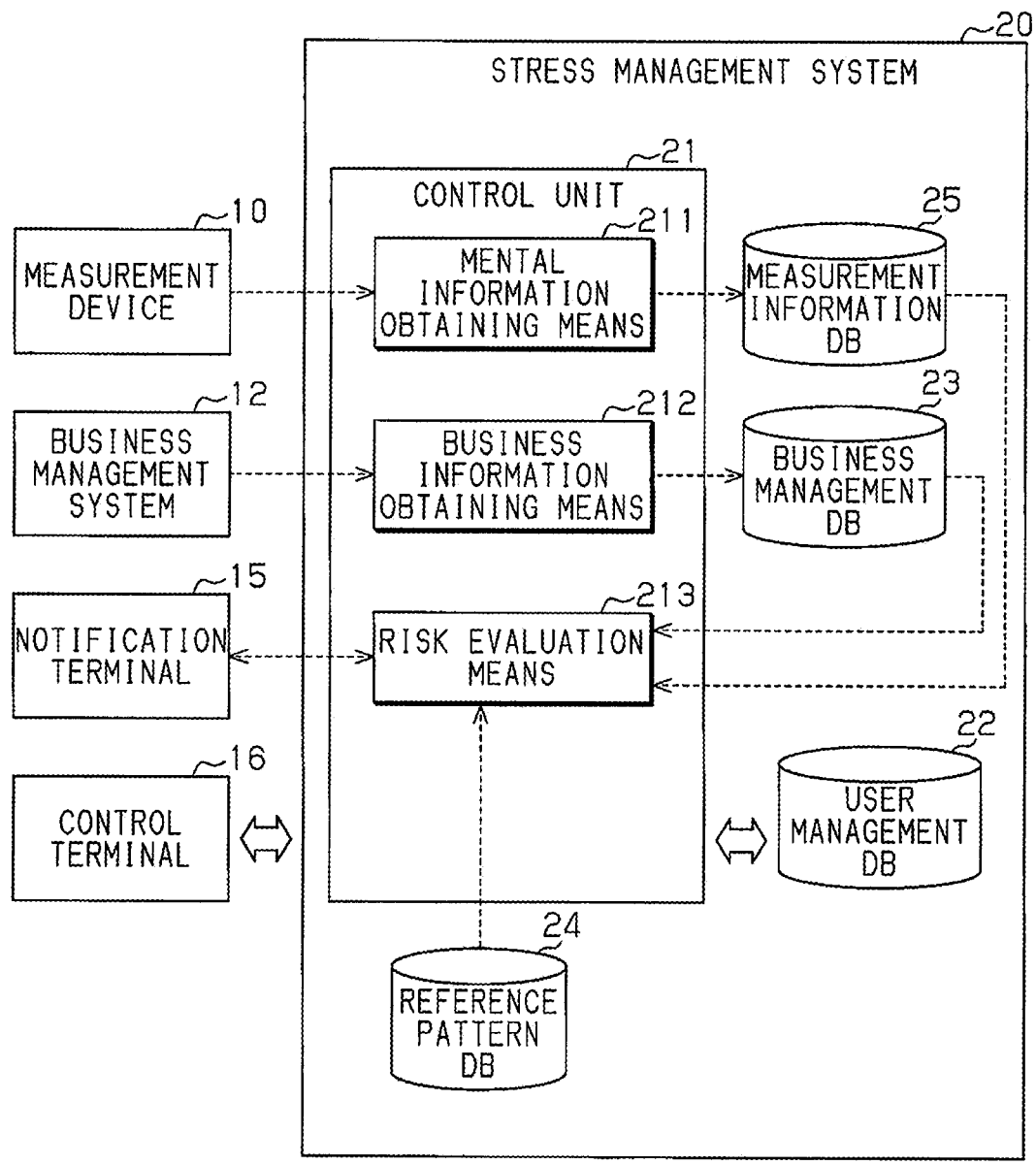
FIG. 1 is a schematic view of a system according to one embodiment of the present invention.

With reference to FIG. 1 to FIG. 7, one embodiment according to the present invention will now be described. The present embodiment will be described as a risk evaluation system for use in evaluating a risk in each member and a business operation by obtaining mental information of members (or individuals in charge) who carry out the business operation collectively. For example, description will be made on the assumption that a group made of an aggregation of individuals shares a target business operation to carry out in such a case as system development. Then, a mental value of a party (which is an individual or a group playing a specific role) is used for risk evaluation. In order to realize this, the present embodiment uses a stress management system 20 connected to a plurality of measurement devices 10 as shown in FIG. 1.

The measurement devices 10 are measurement means (or measurement units) for measuring the stress of each person in charge as mental information of the stress or other factors. The measurement devices 10 measure the stress by a known stress measurement method. For example, there is a method to evaluate the stress by using indexes of visual/motor system reaction (i.e. eye movement such as pupil diameter and blinking and iris light reaction) and indexes of endocrine/immune system reaction (i.e. cortisol in saliva, immunoglobulin, catecholamine and amylase). Then, a measurement method code is allocated to each of the measurement devices 10 in order to identify a measurement method employed in each of the devices.

The stress management system 20 is further connected to a business management system 12, a notification terminal 15 and a control terminal 16.

The business management system 12 is a computer system for managing each business operation. In the present embodiment, the stress management system 20 obtains information of each business operation (such as attributes, structure and plan of business operation, participating members and progress status) from the business management system 12. Information directly input from the control terminal 16 may also be used as information on each business operation.

The notification terminal 15 functions as output means (or output unit) for notifying evaluation results to users or a person in charge and/or an administrator who are engaged in each business operation. For example, for the notification terminal, a computer terminal provided with a display unit composed of a display or other elements and an input unit composed of a keyboard and a pointing device or other elements, an electronic mail distribution function and a mail output device can be used.

The stress management system 20 is a computer system to evaluate a risk based on values measured in the measurement devices 10. The stress management system 20 is provided with a control unit 21, a user management database 22, a business management database 23, a reference pattern database 24 and a measurement information database 25.

The control unit 21 includes control means composed of elements such as a CPU, a RAM and a ROM (not shown) in order to carry out processes described below (i.e. respective processes in a mental information obtaining stage, a business information obtaining stage and a risk evaluation stage or other stages). The control unit 21 is then made to function by risk evaluation programs as mental information obtaining means (or mental information obtaining unit) 211, business information obtaining means (or business information obtaining unit) 212 and risk evaluation means (or risk evaluation unit) 213.

The mental information obtaining means 211 executes a process to obtain mental information from the measurement device 10 to record in a measurement information database 25.

The business information obtaining means 212 executes a process to obtain business management information (such as attributes, structure and plan of business operation, participating members and progress status) input by users from the business management system 12 and/or the control terminal 16 to record in the business management database 23.

The risk evaluation means 213 executes a process to output an evaluation result at timing set by evaluation notification setting means (or evaluation notification setting unit) not shown. As this timing, timing to obtain new measurement information or a predetermined schedule can be used. The risk evaluation means 213 then executes a risk evaluation process by an individual pattern or a group pattern based on information recorded in the measurement information database 25.

Figure 2:
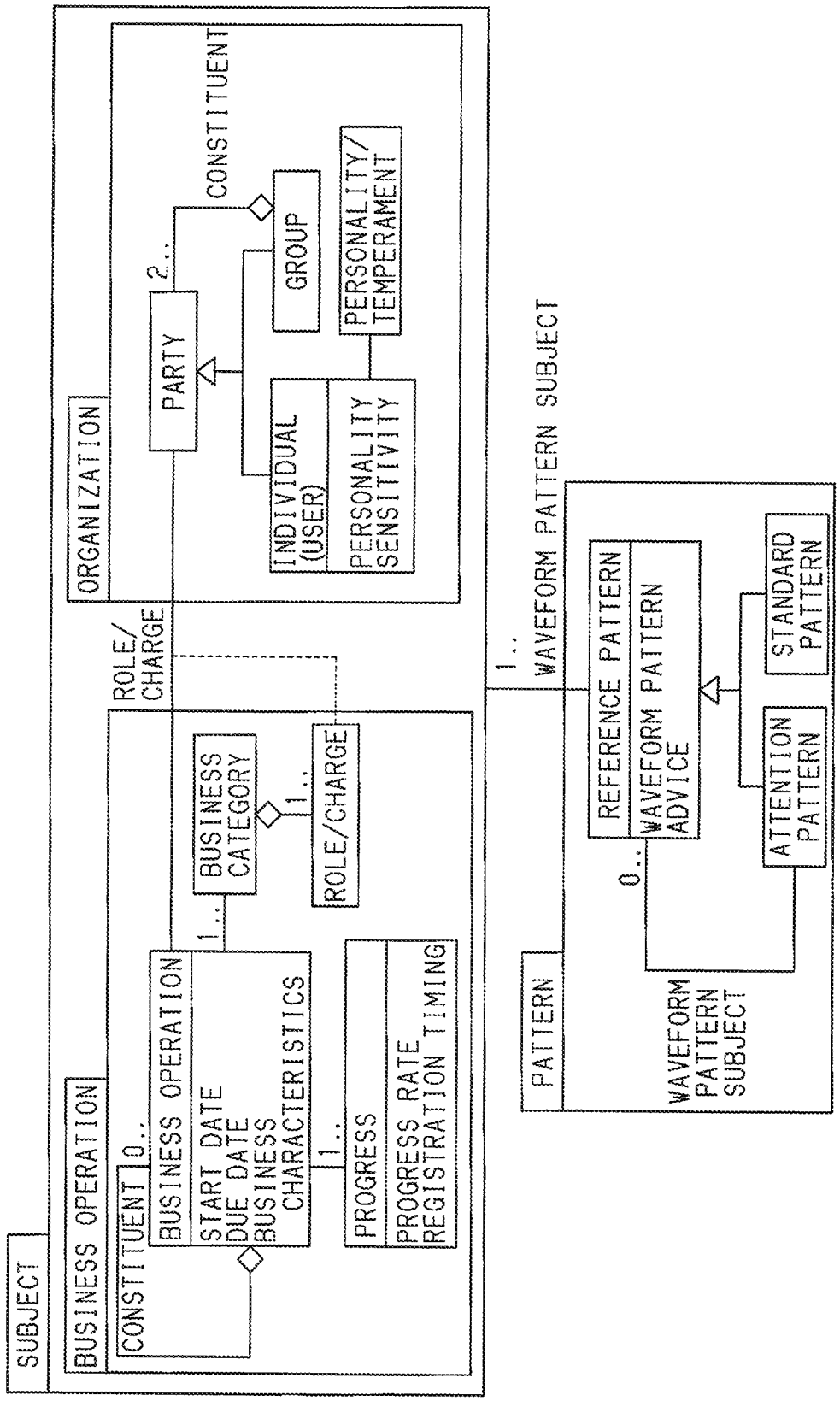
FIG. 2 is a relational diagram of data used in the embodiment of the present invention.

Described next will be data used in the present embodiment by using a class diagram shown in FIG. 2. Packages of "subject" and "pattern" are used. The "subject" package includes packages of "business" and "organization". The "business" package includes "business category" under which "business" information such as a start date, a due date and business characteristics and its business operation fall, "role/charge" particular to the business category, and "progress" information of the business operation. A business operation may have a lower business operation to constitute the business operation. The "organization" package consists of "individual" and "group", or "party" generalizing them. In composition of a group, a role in the group such as "leader" may be allocated. The "individual" includes sensitivity as well as personality and temperament.

The "pattern" package includes a wave generated by component elements of a business operation and/or an organization as well as a combination thereof to be set as a subject. Patterns such as an attention pattern and a standard pattern are included.

Next, each of the databases (22 to 25) for storing data included in this class diagram will be described.

Figure 3A:
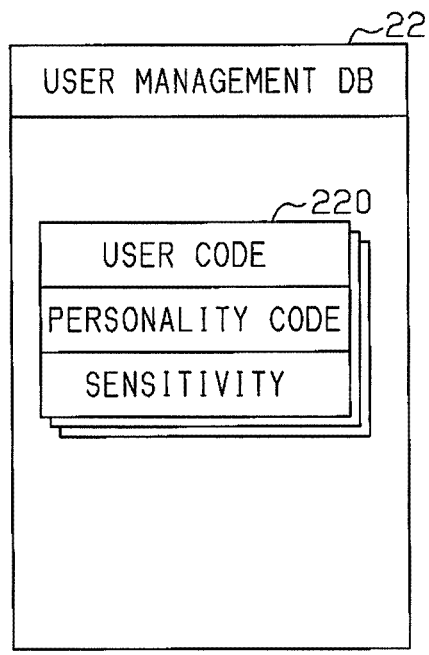
FIG. 3(a) and FIG. 3(b) are explanatory diagrams of data used in the present embodiment, including section (a) for data recorded in a user management database and section (b) for data recorded in a business management database.
Figure 3B:
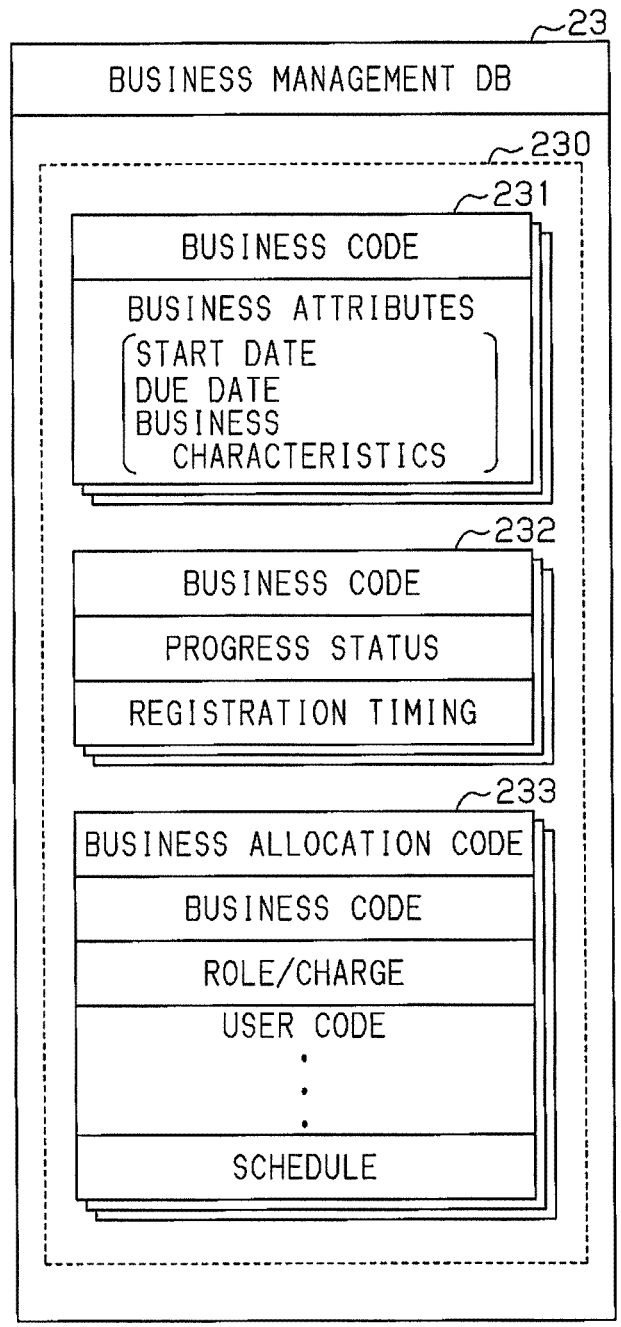

The user management database 22, which functions as user attribute information storage means (or user attribute information storage unit), stores a user management record 220 as shown in FIG. 3(*a*) for managing users of the stress management system 20. The user management record 220 is recorded when a user is registered. The user management record 220 includes data regarding a user code, a personality code and sensitivity.

Recorded in a user code data area is data regarding an identifier to identify a user of the stress management system 20. Based on the user code, contact information (e.g. mail address) of the user can be obtained from a contact management database (not shown).

Recorded in a personality code data area is data regarding an identifier to identify the personality/temperament of the user. Based on the personality code, a correction value to make various kinds of corrections in the comparison to a measured value and a reference pattern can be obtained from a pattern correction database (not shown).

Recorded in a sensitivity data area is data regarding a coefficient to convert a measured value output corresponding to a measurement method into a mental value (or stress intensity). In this data area, sensitivity is recorded to correct measured values measured in the measurement devices 10 for each measurement method code.

In the business management database 23, which functions as business attribute information storage means (or business attribute information storage unit) and business management information storage means (or business management information storage unit), business management data 230 is stored as shown in FIG. 3(*b*) for management of each business operation. The business management data 230 includes a business attribute record 231, a progress status management record 232 and a business allocation record 233.

The business attribute record 231 is recorded when contents of a business operation are registered. The business attribute record 231 includes data regarding a business code and business attribute.

Recorded in a business code data area is data regarding an identifier to identify a business operation. For example, in a case of a system development project, an identifier (or project management code) to identify the project is recorded.

Recorded in a business attribute data area is data regarding an identifier to identify attributes of the business operation. In the present embodiment, a start date, a due date and business characteristics are recorded as business attributes. The business characteristics include parameters regarding urgency, importance and size or other aspects. Based on the parameters of the business attributes, a correction value of a standard pattern for use in risk evaluation can be obtained from a pattern correction database (not shown). If there is a lower business operation, a business code of the lower business operation is included in business characteristics. The business code is then used to develop parameters of the lower business operation such as urgency, importance and size.

The progress status management record 232 is recorded when progress status of each business operation is registered. The progress status management record 232 includes data regarding a business code, progress status and registration timing.

Recorded in a business code data area is data regarding an identifier to identify each business operation.

Recorded in the progress status data area is data regarding an identifier to identify progress status of the business operation. For example, for a business operation concerning system development, information (i.e. process code and progress rate) to specify the start and finish of each phase and process (such as requirement definition, system design, programming and test) carried out in the business operation is recorded. Then, owing to the process code, a person in charge who carries out the business operation and/or a person in charge who finished it can be identified.

Recorded in a registration timing data area is data regarding timing (year, month and date) at which the record was registered.

The business allocation record 233 is recorded when a business allocation for a user is registered. The business allocation record 233 includes data regarding a business allocation code, a business code, a role/charge, a user code and a schedule.

Recorded in a business allocation code data area is data regarding an identifier to identify an allocation of a business operation.

Recorded in a business code data area is data regarding an identifier to identify a business operation carried out by each user.

Recorded in a role/charge data area is data regarding an identifier to identify a role and/or a charge in the business operation. For example, in a business operation concerning system development, a service code such as consultant, system engineer and programmer is recorded.

Recorded in a user code data area is data regarding an identifier to identify a user in the role/charge in the business operation. A business allocation code may also be recorded in this data area.

Recorded in the schedule data area is data regarding timing (year, month and date) at which the business operation is carried out by the role/charge.

Figure 4A:
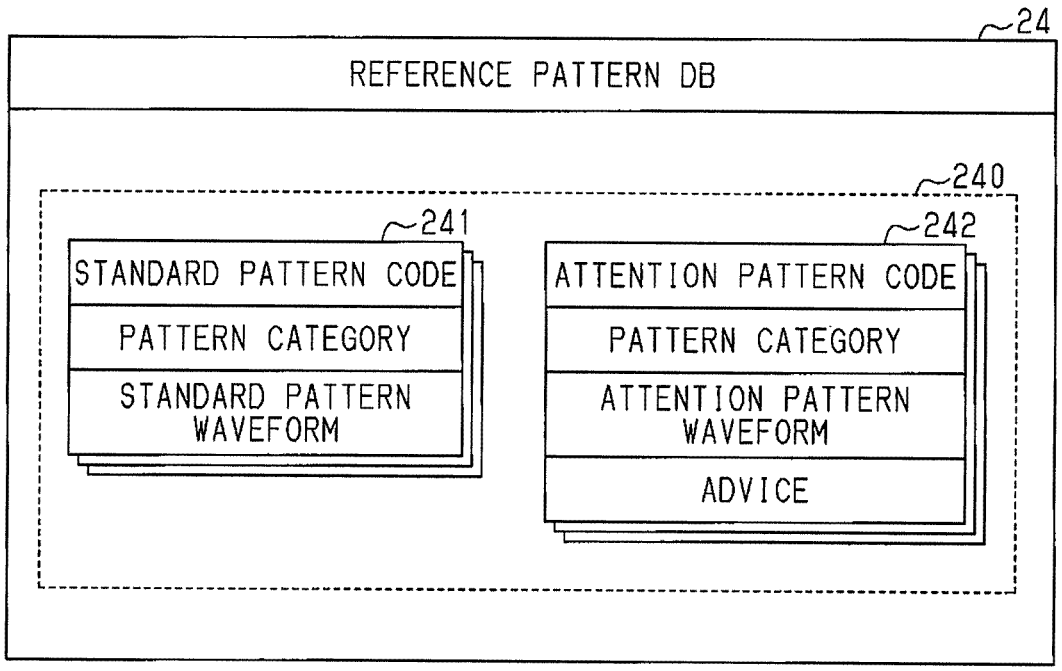
FIG. 4(a) and FIG. 4(b) are explanatory diagrams of data used in the present embodiment, including section (a) for data recorded in a reference pattern database and section (b) for data recorded in a measurement information database.
Figure 4B:
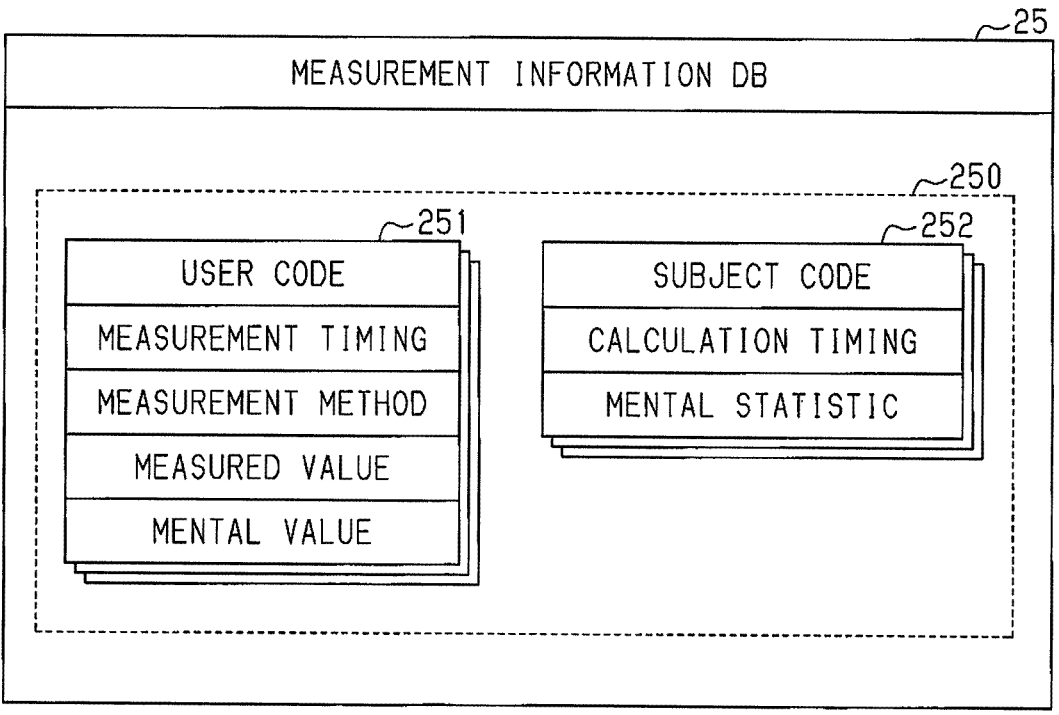

The reference pattern database 24, which functions as pattern information storage means (or pattern information storage unit), records reference pattern data 240 for stress evaluation as shown in FIG. 4(*a*). The reference pattern data 240 consists of a standard pattern management record 241 and an attention pattern management record 242. The standard pattern management record 241 and the attention pattern management record 242 are recorded when a standard pattern and an attention pattern are registered, respectively.

The standard pattern management record 241 includes data regarding a standard pattern code, a pattern category and a standard pattern waveform.

Recorded in a standard pattern code data area is data regarding an identifier to identify each standard pattern.

Recorded in a pattern category data area is data regarding an identifier to identify a category to which the standard pattern belongs. Using the pattern category makes it possible to identify either an individual pattern or a group pattern and in the case of a group pattern, identify which business operation or business allocation the pattern relates to.

Recorded in a standard pattern waveform data area is data regarding a standard stress waveform in a business operation or the like.

For example, a business operation concerning system development has the following waveforms.

"High in downstream": The stress is higher in a programming phase than analysis and design phases.

"High progress": The stress increases as a progress rate becomes higher.

The attention pattern management record 242 includes data regarding an attention pattern code, a pattern category, an attention pattern waveform and an advice.

Recorded in an attention pattern code data area is data regarding an identifier to identify each attention pattern.

Recorded in a pattern category data area is data regarding an identifier (or flag) to identify a category to which the attention pattern belongs. Using the pattern category makes it possible to identify an individual pattern or a group pattern as well as a business operation and a business allocation in a group pattern.

Recorded in an attention pattern waveform data area is data regarding a waveform of a measured value/statistic to which attention should be paid.

For example, an attention pattern independently provided for each party (or individual or group playing a certain role) is classified as follows.

"Continuing at high level": In a wave shown by a measured value/statistic, a period in which a high stress level is continued (i.e. evaluation index) is equal to or more than a reference period.

"Violent fluctuations": In a wave shown by a measured value/statistic, a stress level change within a reference period (i.e. evaluation index) exceeds a reference value and goes up and down violently within a short period of time.

"Separation": In a wave shown by a measured value/statistic, a separation amount relative to a reference pattern corresponding to business attributes and a progress rate (i.e. evaluation index) exceeds a reference value.

In addition, an attention pattern provided for each member who constitutes a group (each member who is a party can be either an individual or a lower group) is classified as follows.

"Outlier": A wave shown by a measured value/statistic suggests the presence of a member who shows a pattern of a value exceeding a permissible range relative to a range calculated by members belonging to the same group.

"Large variations": In a wave shown by a measured value/statistic, the variation of values and patterns of members belonging to the same group (i.e. evaluation index) exceeds a reference value.

Recorded in an advice data area is data regarding an advice provided for each user (i.e. an individual or an administrator of a business operation) when the waveform is detected.

The measurement information database 25, which functions as measurement information storage means (or measurement information storage unit), stores measurement data 250 for managing measured values assumed in the measurement devices 10 and statistics calculated based on the measured values, as shown in FIG. 4(*b*). The measurement data 250 includes a measurement result management record 251 and a statistic management record 252.

The measurement result management record 251 is recorded when a mental value is calculated based on a measured value obtained from the measurement device 10. The measurement result management record 251 includes data regarding a user code, measurement timing, a measurement method, a measured value and a mental value.

Recorded in a user code data area is data regarding an identifier to identify each user.

Recorded in a measurement timing data area is data regarding timing (year, month and date as well as time) at which a measured value for the user was obtained.

Recorded in a measurement method data area is data regarding an identifier (or a measurement method code) to identify a measurement method employed in the measurement device 10, which obtained the measured value.

Recorded in a measured value data area is data regarding the measured value obtained from the measurement device 10.

Recorded in a mental value data area is data regarding an identifier to identify a correction value obtained through correction in accordance with each user.

The statistic management record 252 is recorded when a statistic is calculated based on a measured value of each user who belongs to each business operation. The statistic management record 252 includes data regarding a subject code, calculation timing and a mental statistic.

Recorded in a subject code data area is data regarding an identifier to identify a subject of the statistic. More specifically, a business code or a business allocation code is recorded.

Recorded in a calculation timing data area is data regarding timing (which includes year, month and date) at which the statistic was calculated.

Recorded in a mental statistic data area is data regarding a statistic of a subject shown by a subject code.

The stress management system 20 is further provided with a pattern correction database (not shown). The pattern correction database records a correction value to correct a measured value and a reference pattern in association with a personality code and a correction value to correct a reference pattern in association with parameters of business attributes.

Figure 5:
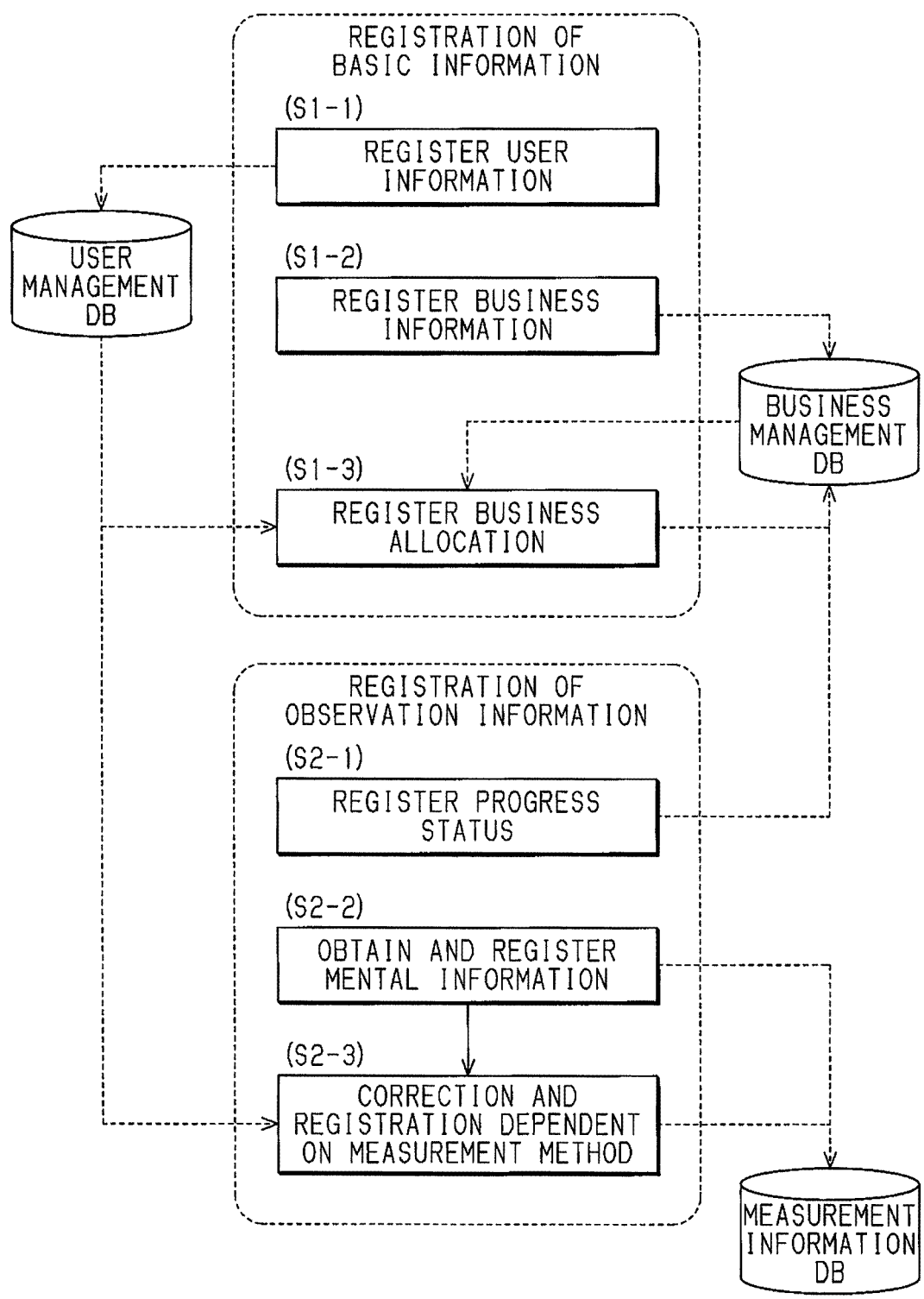
FIG. 5 is an explanatory diagram showing a processing procedure in the present embodiment.
Figure 6:
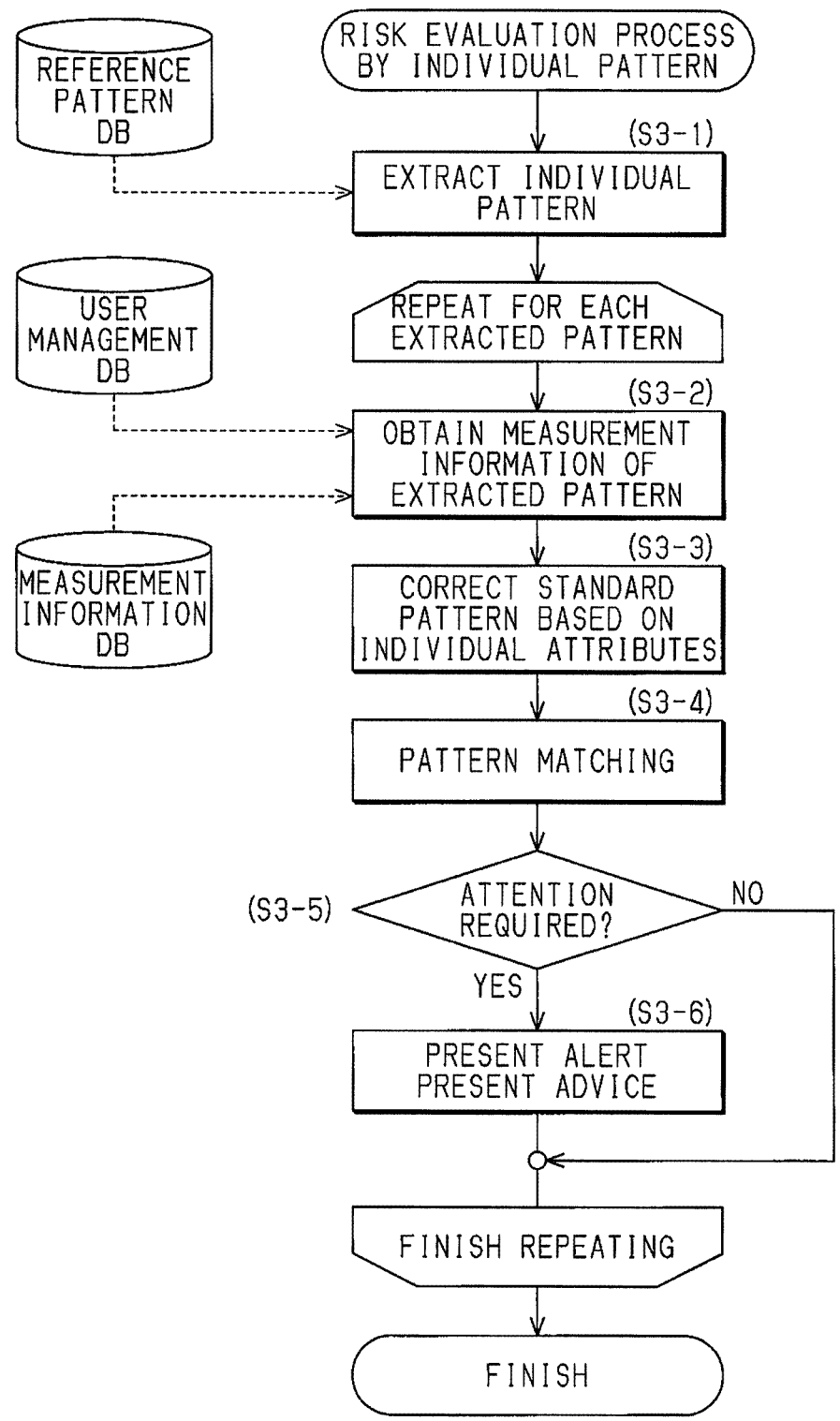
FIG. 6 is an explanatory diagram showing a processing procedure in the present embodiment.
Figure 7:
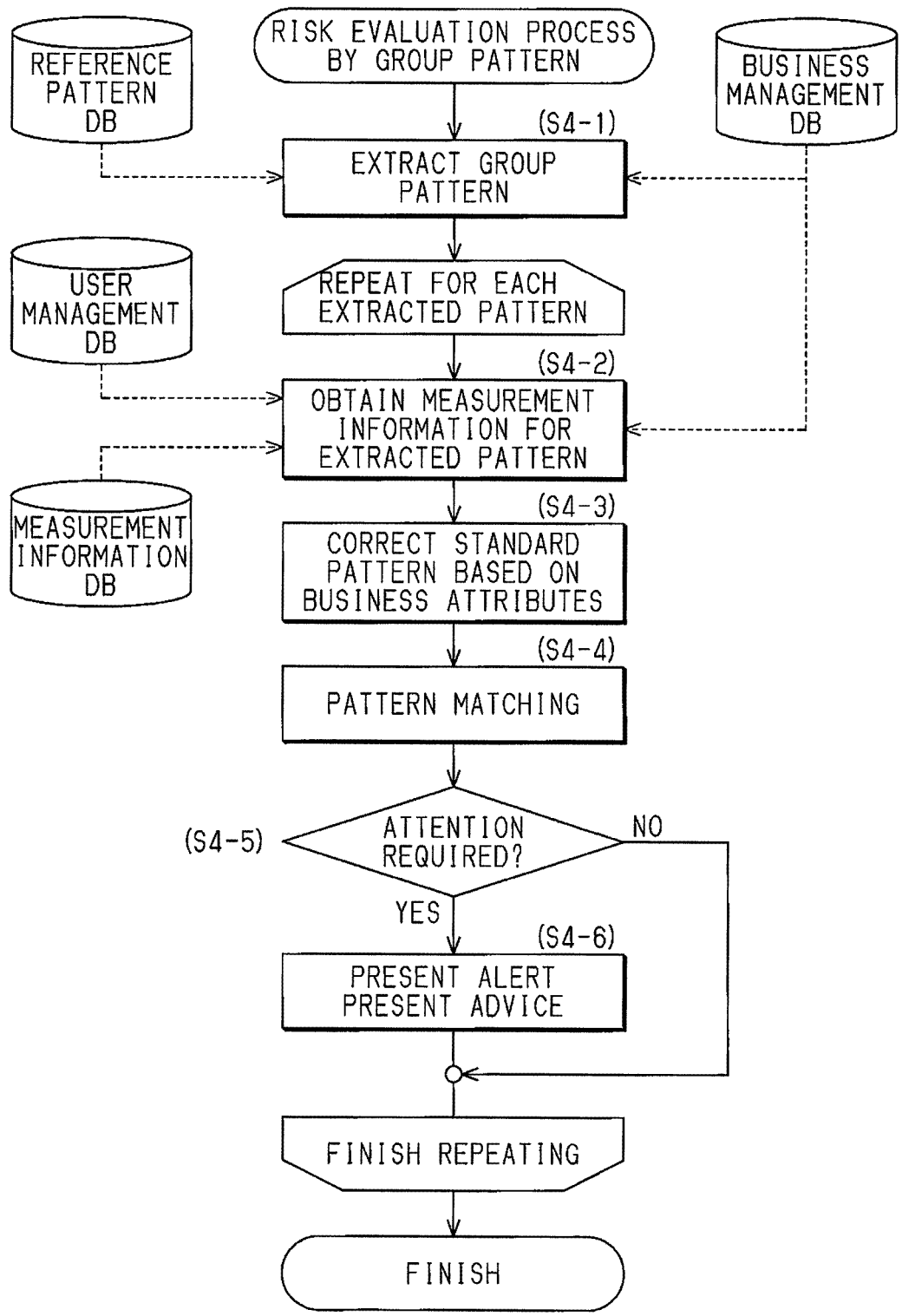
FIG. 7 is an explanatory diagram showing a processing procedure in the present embodiment.

A processing procedure for risk evaluation by using the system structured as stated above will be described with FIG. 5 to FIG. 7. Description will be made in the order from a registration process of basic information to a registration process of observation information, a risk process by an individual pattern and a risk evaluation process by a group pattern.

(Registration of Basic Information)

When the stress management system 20 is used, basic information is registered first. The registration of basic information will be described by using FIG. 5.

In the stress management system 20, a registration process of user information is executed (step S1-1). More specifically, the control terminal 16 is used to transmit a user information registration request for a user who is subjected to risk evaluation to the stress management system 20. The user information registration request includes data regarding a user code, personality and sensitivity. The control unit 21 in the stress management system 20, which has received the user information registration request, registers data obtained from the control terminal 16 in the user management database 22.

Further executed in the stress management system 20 is a registration process of business information (step S1-2). More specifically, the control terminal 16 is used to transmit a business information registration request for a business operation subjected to risk evaluation to the stress management system 20. The business information registration request includes business attribute information (i.e. a business code and business attributes). The control unit 21 in the stress management system 20, which has received the business information registration request, registers data obtained from the control terminal 16 in the business management database 23.

Further executed in the stress management system 20 is a registration process of a business allocation (step S1-3). More specifically, the control terminal 16 is used to transmit a business allocation information registration request for a business operation subjected to risk evaluation to the stress management system 20. The business allocation information registration request includes business allocation information (such as a business code, a role/charge, a user code and a schedule). The control unit 21 in the stress management system 20, which has received the business allocation information registration request, registers data obtained from the control terminal 16 in the business allocation record 233. The control unit 21 may also obtain business operation information in which a user is engaged from the business management system 12 based on a user code. The control unit 21 may also obtain business operation information in which a user is engaged from the business management system 12 based on a business code.

(Registration of Observation Information)

Then, the stress management system 20 obtains observation information for registration in each of the databases. The registration of observation information will be described by using FIG. 5.

The control unit 21 in the stress management system 20 executes a registration process of progress status (step S2-1). More specifically, the business information obtaining means 212 of the control unit 21 periodically accesses the business management system 12 to obtain progress status information associated with each business code. For example, in the case of a business operation concerning system development, a process code to identify a phase/process carried out in each business operation is obtained. The business information obtaining means 212 then registers a process code and a progress rate in the business management database 23 based on the obtained business progress information.

The control unit 21 in the stress management system 20 also executes a process to obtain and register mental information (step S2-2). More specifically, a user inputs a user code in the measurement device 10 for measurement of mental information. In this case, the measurement device 10 transmits a measurement result to the stress management system 20. The measurement result includes a measurement method code, a measured value and a user code. The mental information obtaining means 211 of the control unit 21 in the stress management system 20 generates the measurement result management record 251, in which the measurement result obtained from the measurement device 10 is recorded, and registers it in the measurement information database 25. The control unit 21 in the stress management system 20 may also urge a terminal used by a user to periodically measure mental information. In this case, upon detection of a user who has passed a predetermined interval of time or longer since the last measurement of mental information, contact information in relation to the user (i.e. contact of the user himself or his administrator) is obtained from a contact management database and a message to urge measurement of mental information is output in the notification terminal 15 of the contact.

Next, the control unit 21 in the stress management system 20 executes a correction and registration process dependent on a measurement method (step S2-3). More specifically, the mental information obtaining means 211 of the control unit 21 obtains sensitivity corresponding to a user code and a measurement method code from the user management database 22. The mental information obtaining means 211 then calculates a mental value obtained by correcting a measured value using the sensitivity and registers it in the measurement result management record 251.

(Risk Evaluation Process by Individual Pattern)

Next, a risk evaluation process by an individual pattern will be described by using FIG. 6.

The control unit 21 in the stress management system 20 executes a process to extract an individual pattern (step S3-1). More specifically, the risk evaluation means 213 of the control unit 21 extracts, from the reference pattern database 24, a standard pattern code in which an individual pattern is defined as a pattern category, a standard pattern to which an attention pattern code is given, and an attention pattern.

The control unit 21 in the stress management system 20 then repeats the following processes for each extracted pattern.

The control unit 21 in the stress management system 20 executes a process to obtain measurement information of an extracted pattern (step S3-2). More specifically, the risk evaluation means 213 of the control unit 21 obtains a personality code associated with each user code from the user management record 220 of the user management database 22. The risk evaluation means 213 further obtains a mental value or its transition of each user from the measurement result management record 251 of the measurement information database 25.

Next, the control unit 21 in the stress management system 20 executes a process to correct a standard pattern based on individual attributes (step S3-3). More specifically, the risk evaluation means 213 of the control unit 21 obtains a correction value corresponding to a personality code of each user from a pattern correction database. The risk evaluation means 213 then corrects an extracted standard pattern by using the correction value.

Next, the control unit 21 in the stress management system 20 executes a pattern matching process (step S3-4). More specifically, the risk evaluation means 213 of the control unit 21 compares a corrected standard pattern and a mental value (or its transition) obtained from the measurement information database 25. The risk evaluation means 213 further calculates an evaluation index corresponding to an attention pattern extracted from the reference pattern database 24.

Next, the control unit 21 in the stress management system 20 executes a process to determine whether attention is required (step S3-5). More specifically, the risk evaluation means 213 of the control unit 21 determines "attention required" if the variance of a mental value relative to a corrected standard pattern (i.e. evaluation index) is greater than or equal to a reference value. The risk evaluation means 213 also determines "attention required" if an evaluation index similar to an attention pattern is detected.

If attention required is determined ("YES" in step S3-5), the control unit 21 in the stress management system 20 executes a process to present an alert and present an advice (step S3-6). More specifically, the risk evaluation means 213 of the control unit 21 obtains a contact of the user from a contact management database. Then, the risk evaluation means 213 then presents an alert to the contact. The alert includes a waveform (or transition) of a measured value. The risk evaluation means 213 further obtains an advice corresponding to a detected attention pattern and present the advice. In determination of no attention required ("NO" in step S3-5), the control unit 21 in the stress management system 20 skips the process to present an alert and present an advice (i.e. step S3-6).

(Risk Evaluation Process by Group Pattern)

Next, a risk evaluation process by a group pattern will be described by using FIG. 7.

The control unit 21 in the stress management system 20 executes a process to extract a group pattern (step S4-1). More specifically, the risk evaluation means 213 of the control unit 21 obtains, from the reference pattern database 24, a standard pattern in which a group pattern is defined as a pattern category, a standard pattern to which an attention pattern code is given, and an attention pattern. A group pattern is accompanied by specific business characteristics and/or a particular role/charge (i.e. business characteristics and a role/charge are recorded in a group pattern), a pattern with matching business characteristics and role/charge in the "business management database" is extracted.

Then, the control unit 21 in the stress management system 20 repeats the following processes for each extracted pattern.

The control unit 21 in the stress management system 20 executes a process to obtain measurement information of an extracted pattern (step S4-2). More specifically, the risk evaluation means 213 of the control unit 21 obtains business attributes associated with each business code from the business attribute record 231 of the business management database 23. Furthermore, if a business code is recorded as a pattern category, the risk evaluation means 213 obtains a user code associated with each business code from the business allocation record of the business management database 23. If a business allocation code is recorded as a pattern category, the risk evaluation means 213 obtains a user code associated with the business allocation record in the business management database 23. The risk evaluation means 213 then obtains a mental value associated with the user code (i.e. a mental value of a user involved in the business operation) from the measurement result management record 251 of the measurement information database 25.

Next, the control unit 21 in the stress management system 20 executes a process to correct a standard pattern based on business attributes (step S4-3). More specifically, the risk evaluation means 213 of the control unit 21 obtains a correction value corresponding to business attributes of each business operation from a pattern correction database. The risk evaluation means 213 then corrects an extracted standard pattern by using the correction value.

Next, the control unit 21 in the stress management system 20 executes a pattern matching process (step S4-4). More specifically, the risk evaluation means 213 of the control unit 21 calculates a mental statistic by using a mental value of a user who is involved in the business operation. A mean value is calculated as a statistic. The risk evaluation means 213 then compares a corrected standard pattern and a mental statistic (or its transition). The risk evaluation means 213 further calculates an evaluation index corresponding to an attention pattern extracted from the reference pattern database 24.

Next, the control unit 21 in the stress management system 20 executes a process to determine whether attention is required (step S4-5). More specifically, the risk evaluation means 213 of the control unit 21 determines "attention required" if the variance of a mental statistic relative to a corrected standard pattern (i.e. evaluation index) is greater than or equal to a reference value. The risk evaluation means 213 also determines "attention required" if an evaluation index that matches with an attention pattern is detected.

If attention required is determined ("YES" in step S4-5), the control unit 21 in the stress management system 20 executes a process to present an alert and present an advice (step S4-6). More specifically, the risk evaluation means 213 of the control unit 21 identifies a user code of a person responsible for the business operation from the business allocation record 233. Next, the risk evaluation means 213 obtains a contact of the person responsible from the contact management database. Then, the risk evaluation means 213 presents an alert to the contact. In this case, the alert may include information of a user who forms an attention pattern. The risk evaluation means 213 further obtains an advice corresponding to an attention pattern from the reference pattern database 24 and presents the advice. In determination of no attention required ("NO" in step S4-5), the control unit 21 in the stress management system 20 skips the process to present an alert and present an advice (i.e. step S4-6).

According to the present embodiment, following advantages can be obtained.

(1) In the present embodiment, a risk evaluation process is executed by using an individual pattern. Therefore, a situation where attention is required can be determined by using transition of mental information of individuals. When the stress is high, the quality and productivity of a work operation carried out by each individual may possibly deteriorate. Such possibility can be detected promptly through observation of the stress or other factors of each user. Continuous observation of the stress or other factors makes it possible to perceive the deterioration risk of a mental state of each user.

(2) In the present embodiment, a risk evaluation process is executed by using a group pattern. Therefore, a situation where attention is required can be determined by using mental information of a group which is an aggregate of individuals. In the present embodiment, the risk of business operations can be "visualized" by using a plurality of members participating in a group (e.g. a specific business operation such as a project) as sensors. Members participating in a specific business operation are actually feeling the reality of the business operation. There is a research that suggests that the biggest factor of the stress felt by participating members is a business operation. If participating members have feelings such as "the business operation is not working well" and "with the situation as it is, the business operation will fail", their stress would increase. That is, continuous observation of the mental state (such as stress) of participating members makes it possible to visualize the risk on business operations in real time.

Moreover, when a business code is recorded as a pattern category in the process to obtain measurement information of an extracted pattern (i.e. step S4-2), a user code associated with each business code is obtained from the business allocation record of the business management database 23. When a business allocation code is recorded as a pattern category, a user code associated with the business allocation record of the business management database 23 is obtained. Then, the risk evaluation means 213 obtains a mental value associated with the user code from the measurement result management record 251 of the measurement information database 25. The mental value is used for the control unit 21 in the stress management system 20 to execute a pattern matching process (i.e. step S4-4). When a group pattern is applied to a system (or a business operation) composed of a plurality of subsystems (or lower business operations), there are two types of constituent elements (i.e. members) as follows.

Subsystem

Persons (or members) involved in a system (including a subsystem and a sub-subsystem or the like)

It is therefore possible to analyze the stress or other factors of members based on constituent information of a business operation such as role sharing. Accordingly, risk evaluation on business operations can be realized in real time such as evaluating where a risk is involved on a business operation and how a business risk spreads.

(3) In the present embodiment, the control unit 21 in the stress management system 20 executes a process to correct a standard pattern based on individual attributes (i.e. step S3-3). It is therefore possible to perform precise pattern matching in accordance with an individual situation.

(4) In the present embodiment, the control unit 21 in the stress management system 20 executes a process to correct a standard pattern based on business attributes (i.e. step S4-3). It is therefore possible to perform precise pattern matching in accordance with a business situation.

(5) The reference pattern database 24 records the reference pattern data 240 for stress evaluation. Attention patterns of individuals in a group are recorded. Therefore, for instance, if a mental value of an individual belonging to the group exceeds a permissible range in comparison with a mental statistic of the group, an alert can be presented. Accordingly, an individual who shows a different tendency from that of the mental statistic of the group can be detected.

Each of the above embodiments may be modified as follows.

In the above embodiment, the mental information obtaining means 211 registers measurement results obtained from the measurement devices 10 in the measurement information database 25. The mental information obtaining means 211 may obtain a measurement result at predetermined timing. In this case, the mental information obtaining means 211 is provided with a function to determine timing to obtain a measurement result. The obtaining timing can be classified as follows, with further possibility of combining a plurality of timing including manual timing.

Continuous: Mental information is measured as continuous data without a break.

Periodical: Mental information is measured intermittently at designated intervals such as hourly, daily and weekly.

At each event: Mental information is measured by using an event such as a progress meeting (in conjunction with a scheduler) as a starting point.

At each authentication: Mental information is measured at authentication (in conjunction with biometric authentication).

In the above embodiment, the measurement devices 10 measure the stress by using indexes of visual/motor system reaction and indexes of endocrine/immune system reaction. The stress measurement method is not limited to the above index measurement. For example, the measurement devices 10 do not necessarily have to be concrete measurement devices. The measurement devices 10 may receive mental information output from a concrete measurement device. Questionnaires and/or questionnaire surveys may also be carried out for subjective/cognitive reaction (questioning). It is also possible to use, as a measurement technique for physiological index (i.e. biometric information), indexes of central nervous system reaction (i.e. brain wave), indexes of autonomic nervous system reaction (i.e. heart rate variability, blood pressure, fingertip pulse, breathing activity, skin temperature, perspiration, Ryodoro (or highly conductive path or current)), emotional indexes (voice), and behavioral reaction (i.e. measurement with a focus on items such as reaction time and workload). As a behavioral reaction index, the number of times/frequency of leaving the desk and the strength and fluctuation of keystrokes of the keyboard can also be used. The number of times of leaving the desk can be calculated by, for example, arranging a pressure sensor on the seat of each user or in cooperation with an entry/exit management system. The strength and fluctuation of keystrokes of the keyboard can also be calculated by arranging a pressure sensor in the keyboard.

In the above embodiment, the reference pattern database 24 records an attention pattern. The attention pattern is not limited to the above example. For example, an attention pattern based on the role of a business operation or the like may also be used. Usable examples include an attention pattern indicating a situation where the difference of the stress between an administrator and a person in charge is reversed or diverge and an attention pattern indicating a situation where the difference of the stress between a designer and a programmer is reversed or diverge. In this case, role/charge data recorded in the business allocation record 233 is used. Then, the control unit 21 identifies a role/charge of each user and compares mental values corresponding to the role/charge. Therefore, risk evaluation can be realized in such cases that communication is insufficient and all the stresses are shifted on to lower processes.

In the above embodiment, the control unit 21 in the stress management system 20 executes a process to correct a standard pattern based on individual attributes (i.e. step S3-3). A life event may be used to correct a standard pattern. In this case, a correction value corresponding to a life event is recorded in the pattern correction database. For example, for a user whose attribute information is recorded in the user management database 22 that his/her mood is dependent on the calendar (or days of a week), a standard pattern is corrected by using calendar information at measurement timing. In addition, when personnel change information of a user is obtained from a personnel management system, a standard pattern is corrected based on a correction value corresponding to a life event that is the personnel change. A standard pattern may also be corrected by a combination of these situations.

In the above embodiment, when attention required is determined (i.e. "YES" in steps S3-5 and S4-5), the control unit 21 in the stress management system 20 executes a process to present an alert and present an advice (i.e. steps S3-6 and S4-6). An alert may also be presented by a combination of a plurality of patterns. More specifically, in order to present an alert, a combination of pattern codes is registered in the reference pattern database 24. Therefore, an alert can be presented by using various conditions.

In the above embodiment, a standard pattern is corrected based on individual attributes and business attributes for pattern matching (i.e. steps S3-3 and S4-3). As long as correction is made according to attributes, correction is not limited to a standard pattern. For example, correction of a measured value and a statistic as well as correction of a comparison result may also be made.

In the above embodiment, "outlier" and "large variation" are used as an attention pattern for each individual belonging to a group. There is no restriction on evaluation of the pattern. For example, in the statistic management record 252, "distribution", "similarity", "propagation" and "reverse" can also be evaluated in accordance with transition of a mental statistic.

"Distribution": For distribution of the stress within a group such as "2:6:2 law" and "Pareto's law", a pattern is compared to a preset standard pattern so as to determine whether a separation amount relative to the standard pattern (i.e. evaluation index) exceeds a reference value. A different pattern may also be used for distribution depending on the size of a party.

"Similarity": A pattern of a party (or individual or group) is compared to an average pattern obtained from similar situations of the same kind of business operations in the past so as to determine whether a separation amount relative to the average pattern (i.e. evaluation index) exceeds a reference value.

"Propagation": It is determined based on a wave change (i.e. evaluation index) whether a high stress is propagated to other members or a member involved in another business operation.

"Reverse": It is determined based on a wave change (i.e. evaluation index) whether a party of a high stress and a party of a low stress are switched. Particularly for a leader and members belonging to the same business operation or among business operations whose roles are different, the stress is determined by using a mental value change.

For these evaluations, the stress management system 20 is provided with a relevant information database in which the correlation (e.g. the relationship between a boss and a subordinate, the relationship between a preceding business group and a succeeding business group and the relationship among business-related groups) of parties (individuals or groups playing a specific role) is recorded. The relevant information database records information showing relevance of identifiers (or user codes or business codes) to identify parties being relevant to each other.

In the case of "distribution", a standard stress distribution pattern is recorded in the reference pattern database 24. Then, the control unit 21 in the stress management system 20 identifies members (or individuals or groups) to constitute a party in the relevant information database. Next, the control unit 21 obtains a mental value of each constituent member and calculates distribution in the party. The control unit 21 then compares the distribution to the standard stress distribution and calculates a separation degree (e.g. deviation in the distribution). Then, if the separation degree exceeds a reference value, the control unit 21 determines "attention required".

In the case of "similarity", the control unit 21 in the stress management system 20 identifies similar business operations that are relevant to each other in business operations subjected to evaluation in the relevant information database. Then, for an identified business operation, a business code of an already finished business operation is extracted from the business management database 23. Next, the control unit 21 uses the measurement information database 25 to calculate a pattern waveform of a mental value of the past similar business operation (e.g. average pattern waveform) for comparison with a pattern of the business operation subjected to evaluation. If a separation degree of a pattern waveform of the business operation subjected to evaluation relative to the past pattern waveform exceeds a reference value, the control unit 21 determines "attention required".

In the case of "propagation", the control unit 21 in the stress management system 20 identifies a party (i.e. attention party) whose stress value (or mental value or mental statistic) is recorded as being higher than a standard pattern waveform. The control unit 21 then identifies a relevant party that is relevant to the attention party by using the relevant information database. If a mental value or a mental statistic of the relevant party increases to follow a mental value of the attention party, the control unit 21 determines "attention required".

In addition, in the case of "reverse", the control unit 21 in the stress management system 20 obtains a mental value (including a mental statistic) of an attention party and a mental value of a relevant party that is relevant to the attention party. If the mental values of the attention party and the relevant party are reversed later in the relation of size, the control unit 21 determines "attention required".

Particularly in the cases of "propagation" and "reverse", timing to evaluate these cases is often detected before or after a meeting. Therefore, the control unit 21 obtains meeting timing from a schedule database in which meeting schedules of members are recorded, and evaluates "propagation" and "reverse" before or after the meeting timing.

Evaluating mental information in a group under these various kinds of the patterns makes it possible to draw attention through understanding of the situation of members and organizations.

In the above embodiment, the control unit 21 in the stress management system 20 executes a process to present an alert and present an advice (i.e. step S4-6). More specifically, an alert is presented to a contact by the risk evaluation means 213. "Attention required" can be a "degree of risk" corresponding to a degree (such as a degree of separation relative to a standard pattern and a degree of similarity relative to an attention pattern).

In the above embodiment, the reference pattern data 240 is preregistered in the reference pattern database 24 for stress evaluation. The reference pattern includes a standard pattern and an attention pattern. In addition, a new attention pattern may also be calculated in the case of a problem arising in a business operation by obtaining observation information of individuals or groups involved in the business operation. In this case, a predetermined permissible range relative to a standard pattern is stored in the stress management system 20. Then, if information of a business operation with a problem is obtained, the control unit 21 in the stress management system 20 identifies a party relevant to the business operation by using the business management database 23. Next, the control unit 21 obtains observation information of the party (or individual or group) from the measurement information database 25. If a waveform pattern exceeding a permissible range is detected in the observation information, the control unit 21 specifies the pattern as an attention pattern so as to record in the reference pattern database 24. It is also possible to identify an individual or a group whose observation information changes prior to other individuals or groups for use as a sensor to the risk. Therefore, a new attention pattern can be generated from empirical rules based on observation information.

In the above embodiment, the user management database 22, which functions as user attribute information storage means, stores the user management record 220 for management of users of the stress management system 20. The user management record 220 includes data regarding a user code, a personality code and sensitivity. Personality and sensitivity may be set for not only individuals but also groups. In this case, for instance, a personality code and sensitivity of a group (or aggregate) belonging to the business operation are recorded in association with a business management code in the business management database 23. Further, the pattern correction database records a correction value to correct a measured value and a reference pattern in association with a personality code of a group. A correction value and sensitivity corresponding to the personality code are used to correct a mental statistic of the group. Such a personality code and sensitivity of the group can be calculated by an entire structure pattern obtained from a combination of attributes (such as the personality code and the sensitivity) of individuals belonging to the group. It is also possible to set a value (or nature) specific to a group, which is different from the aforementioned calculation result, for the personality code and the sensitivity of the group. Owing to the above configuration, risk evaluation can be carried out by taking the personality and the sensitivity as an aggregate into consideration instead of a simple collection of individuals.

DESCRIPTION OF THE REFERENCE NUMERALS

10: MEASUREMENT DEVICE
12: BUSINESS MANAGEMENT SYSTEM
15: NOTIFICATION TERMINAL
16: CONTROL TERMINAL
20: STRESS MANAGEMENT SYSTEM
21: CONTROL UNIT
211: MENTAL INFORMATION OBTAINING MEANS
212: BUSINESS INFORMATION OBTAINING MEANS
213: RISK EVALUATION MEANS
22: USER MANAGEMENT DATABASE
23: BUSINESS MANAGEMENT DATABASE
24: REFERENCE PATTERN DATABASE
25: MEASUREMENT INFORMATION DATABASE

The invention claimed is:

1. A method for detecting an abnormal condition of mental stress in a group of subjects engaged in a business operation carried out collectively by the subjects of the group, the method comprising:

obtaining and storing constituent information of the business operation carried out by the group and each of the subjects of the group engaged in the business operation, said constituent information including progress status of the business operation from a first time period to a second time period;

measuring with a measurement device that measures at least one parameter selected from the group consisting of a physiological parameter, an emotional parameter and a behavioral reaction parameter to determine stress information of each of the subjects;

determining transition of mental information for each of the subjects in the group from the first period to the second period from the determined stress information of each of the subjects;

calculating a transition of a mental statistic of the group using the transition of mental information measured for each of the subjects of the group;

comparing the transition of mental information of each of the subjects to a reference pattern for personnel stored in a reference pattern database, wherein the reference pattern for personnel includes a standard pattern for personnel and an attention pattern for personnel, the standard pattern for personnel including a standard pattern waveform regarding a standard stress waveform in the business operation, the attention pattern for personnel including an attention pattern waveform regarding a waveform of a measured value of mental information to which attention should be paid;

obtaining, when the variance of the transition of mental information of at least one subject relative to the standard pattern for personnel is greater than or equal to a reference value or when the transition of mental information of at least one subject includes an evaluation index that matches with the attention pattern for personnel, a contact of the at least one object from a contact management database;

outputting automatically an alert including an advice to the contact of the at least one object;

comparing the transition of the mental statistic of the group to a reference pattern for group stored in the reference pattern database, wherein the reference pattern for group includes a standard pattern for group and an attention pattern for group, the standard pattern for group including a standard pattern waveform regarding a standard stress waveform in the business operation, the attention pattern for group including an attention pattern waveform regarding a waveform of a measured value of mental information to which attention should be paid;

obtaining, when the variance of the transition of the mental statistic of the group relative to the standard pattern for group is greater than or equal to a reference value or when the transition of the mental statistic of the group includes an evaluation index that matches with the attention pattern for group, a contact of a person responsible for the business operation from the contact management database; and outputting automatically an alert including an advice to the contact of the person responsible.

2. The method of claim 1, wherein the measured parameter is a physiological parameter.

3. The method of claim 1, further comprising:

obtaining a correction value corresponding to a personality code of each object from a pattern correction database to correct the standard pattern for personnel by using the obtained correction value; and obtaining a correction value corresponding to a business attribute of the business operation from the pattern correction database to correct the standard pattern for group by using the obtained correction value.

4. A system for detecting an abnormal condition of mental stress in a group of subjects engaged in a business operation carried out collectively by the subjects of the group, the system comprising:

a management database configured to obtain and store constituent information of the business operation carried out by the group and each of the subjects of the group engaged in the business operation, said constituent information including progress status of the business operation from a first time period to a second time period;

a measurement device that measures at least one parameter selected from the group consisting of a physiological parameter, an emotional parameter and a behavioral reaction parameter to determine stress information of each of the subjects;

a control unit including a CPU, wherein the control unit is configured to:

determine transition of mental information for each of the of the subjects in the group from the first period to the second period from the determined stress information of each of the subjects;

calculate a transition of a mental statistic of the group using the transition of mental information measured for each of the subjects of the group; and compare the transition of mental information of each of the subjects to a reference pattern for personnel stored in a reference pattern database, wherein the reference pattern for personnel includes a standard pattern for personnel and an attention pattern for personnel, the standard pattern for personnel including a standard pattern waveform regarding a standard stress waveform in the business operation, the attention pattern for personnel including an attention pattern waveform regarding a waveform of a measured value of mental information to which attention should be paid;

obtain, when the variance of the transition of mental information of at least one subject relative to the standard pattern for personnel is greater than or equal to a reference value or when the transition of mental information of at least one subject includes an evaluation index that matches with the attention pattern for personnel, a contact of the at least one object from a contact management database;

output automatically an alert including an advice to the contact of the at least one object;

compare the transition of the mental statistic of the group to a reference pattern for group stored in the reference pattern database, wherein the reference pattern for group includes a standard pattern for group and an attention pattern for group, the standard pattern for group including a standard pattern waveform regarding a standard stress waveform in the business operation, the attention pattern for group including an attention pattern waveform regarding a waveform of a measured value of mental information to which attention should be paid;

obtain, when the variance of the transition of the mental statistic of the group relative to the standard pattern for group is greater than or equal to a reference value or when the transition of the mental statistic of the group includes an evaluation index that matches with the attention pattern for group, a contact of a person responsible for the business operation from the contact management database; and output automatically an alert including an advice to the contact of the person responsible.

5. The system of claim 4, wherein the measured parameter is a physiological parameter.

6. The system of claim 4, wherein the control unit is further configured to:

obtain a correction value corresponding to a personality code of each object from a pattern correction database to correct the standard pattern for personnel by using the obtained correction value; and obtain a correction value corresponding to a business attribute of the business operation from the pattern correction database to correct the standard pattern for group by using the obtained correction value.

* * * * *